(12) United States Patent
Bulumulla et al.

(10) Patent No.: US 9,069,998 B2
(45) Date of Patent: Jun. 30, 2015

(54) DETERMINING ELECTRICAL PROPERTIES OF TISSUE USING MAGNETIC RESONANCE IMAGING AND LEAST SQUARED ESTIMATE

(71) Applicant: General Electric Company, Schenectady, NY (US)

(72) Inventors: Selaka Bandara Bulumulla, Nishayuna, NY (US); Ileana Hancu, Clifton Park, NY (US); Seung-Kyun Lee, Cohoes, NY (US)

(73) Assignee: General Electric Company, Niskayuna, NY (US)

( * ) Notice: Subject to any disclaimer, the term of this patent is extended or adjusted under 35 U.S.C. 154(b) by 443 days.

(21) Appl. No.: 13/652,231

(22) Filed: Oct. 15, 2012

(65) Prior Publication Data

US 2014/0105476 A1    Apr. 17, 2014

(51) Int. Cl.
| G06K 9/00 | (2006.01) |
| G06K 9/32 | (2006.01) |
| G06K 9/34 | (2006.01) |
| G06T 11/00 | (2006.01) |

(52) U.S. Cl.
CPC ........... *G06K 9/00* (2013.01); *G06K 9/3233* (2013.01); *G06K 9/342* (2013.01); *G06T 11/003* (2013.01)

(58) Field of Classification Search
None
See application file for complete search history.

(56) References Cited

U.S. PATENT DOCUMENTS

| 5,995,863 | A | * | 11/1999 | Farace et al. ............... 600/410 |
| 6,026,173 | A | * | 2/2000 | Svenson et al. ............ 382/131 |
| 6,219,440 | B1 | * | 4/2001 | Schaff et al. ............... 382/128 |
| 7,259,558 | B2 |  | 8/2007 | Bieri et al. |
| 8,076,939 | B2 |  | 12/2011 | Setsompop et al. |
| 2010/0290675 | A1 | * | 11/2010 | Wexler et al. ............... 382/109 |
| 2012/0139541 | A1 |  | 6/2012 | Weiss et al. |
| 2013/0018591 | A1 | * | 1/2013 | Grzegorczyk ............... 702/19 |

FOREIGN PATENT DOCUMENTS

WO    2011086512 A1    7/2011

OTHER PUBLICATIONS

Joines et al., "A Comparison Using Tissue Electrical Properties and Temperature Rise to Determine Relative Absorption of Microwave Power in Malignant Tissue", Medical Physics, vol. 16, Issue 6, pp. 840-844, Nov.-Dec. 1989.

Farace et al., "An Automated Method for Mapping Human Tissue Permittivities by MRI in Hyperthermia Treatment Planning", Physics in Medicine and Biology, vol. 42, Issue 11, 1997.

Novotny et al., "Assessment of the Accuracy of Stereotactic Target Localization Using Magnetic Resonance Imaging: A Phantom Study", Journal of Radiosurgery, vol. 1, Issue 2, pp. 99-111, 1998.

(Continued)

*Primary Examiner* — Avinash Yentrapati
(74) *Attorney, Agent, or Firm* — Melissa K. Dobson

(57) ABSTRACT

Exemplary embodiments of the present disclosure are directed to estimating an electrical property of tissue using MR images. Complex values having real components and imaginary components are generated and are associated with pixels in one or more MR images that corresponding to a region of tissue for which the electrical property is constant. An estimated value of the electrical property for the region of tissue is determined based on a least squared error estimation applied to the complex values.

20 Claims, 5 Drawing Sheets

(56) References Cited

OTHER PUBLICATIONS

Yang et al., "Manipulation of Image Intensity Distribution At 7.0 T: Passive RF Shimming and Focusing With Dielectric Materials", Journal of Magnetic Resonance Imaging, vol. 24, Issue 1, pp. 197-202, Jul. 2006.

Zhang et al., "Imaging Electrical Properties of the Human Brain Using a 16-channel Transceiver Array Coil at 7T", Proceedings of the International Society for Magnetic Resonance in Medicine, vol. 19, pp. 126, 2011.

Geeter et al., "A DTI-based Model for TMS using the Independent Impedance Method with Frequency-dependent Tissue Parameters", Physics in Medicine and Biology, vol. 57, Issue 8, pp. 2169-2188, Apr. 21, 2012.

\* cited by examiner

DETERMINING ELECTRICAL PROPERTIES OF TISSUE USING MAGNETIC RESONANCE IMAGING AND LEAST SQUARED ESTIMATE

STATEMENT AS TO FEDERALLY SPONSORED RESEARCH & DEVELOPMENT

This invention was made with Government support under contract number R01CA154433 awarded by the National Institutes of Health through the National Institute of Biomedical Imaging and Bioengineering. The Government has certain rights in the invention.

BACKGROUND

Magnetic Resonance Imaging (MRI) or Nuclear Magnetic Resonance (NMR) imaging generally provides spatial discrimination of resonant interactions between radio frequency (RF) waves on nuclei in a magnetic field. Specifically, MRI utilizes hydrogen nuclear spins of the water molecules in the human body, which are polarized by a strong, uniform, static magnetic field, commonly referred to as $B_0$ or the main magnetic field. When a substance, such as human tissue, is subjected to the main magnetic field, the individual magnetic moments of the spins in the tissue attempt to align with the main magnetic field. When excited by an RF wave, the spins precess about the main magnetic field at a characteristic Larmor frequency. Signals are emitted by the excited spins, which are processed to generate Magnetic Resonance (MR) images of the subject.

Electrical properties of substances, such as human tissue, exposed to MRI can provide insight into a response of the substances to such imaging. For example, a determination of the electrical properties of tissue including conductivity and permittivity are useful in estimating local RF power deposition (also known as local specific absorption rate or SAR) during acquisition of MR images. The electrical properties of tissue can also be useful in discriminating between malignant and healthy tissue (e.g., malignant tissue has been shown to have higher permittivity and conductivity than surrounding healthy tissue). The electrical properties of tissue are also required for treatment planning of therapeutic applications of heat using radio frequency, e.g., RF hyperthermia.

Determining the electrical properties of tissue in-vivo using MRI has posed several problems due to the inability to directly measure the phase of the receive RF magnetic field $B_1^-$ and the phase of the transmit RF magnetic field $B_1^+$. To overcome this limitation, conventional approaches using MRI have estimated the electrical properties of tissue using the transmit RF magnetic field $B_1^+$, for example, by mapping the amplitude of the transmit RF magnetic field and approximating the phase of the transmit magnetic field. Conventional MR-based electrical property measurement techniques typically rely on mapping the transmit RF field $B_1^+$, by attempting to eliminate the effect of the receive RF field $B_1^-$ from the MR images used for the measurements. The amplitude of $B_1^+$ can be obtained using various approaches, such as Bloch-Siegert $B_1^+$ mapping or the double-angle method. The phase of $B_1^+$, on the other hand, is generally more difficult to separate from the phase of $B_1^-$. Methods have been proposed to approximate the phase of $B_1^+$. Using conventional methods, a complex map of $B_1^+$ is formed and the map is subjected to Laplacian operation to produce $k^2$ (complex wave vector) maps and subsequently electrical properties maps.

While conventional approaches have provided techniques for estimating the electrical properties of tissue based on mapping the amplitude of $B_1^+$ and approximating the phase of $B_1^+$, implementations of conventional approaches to generating electrical properties maps are vulnerable to poor results due to noise in B1+ data. This has been addressed by using larger regions to calculate Laplacian operation (e.g. skip factors which consider data points far apart, resulting in differences that are larger than noise terms, increasing the overall SNR of the calculation)

Typically, the use of such skip factors requires a larger area for the estimation of the Laplacian at each pixel location, which can reduce the resolution of the images corresponding to the electrical properties. In other approaches, non-physical values (e.g. negative conductivity) resulting from noise in B1 data have been discarded. The missing pixels were replaced by average values in a local region. In yet other efforts, smoothing of B1+ data have been carried out to remove noise. These approaches can lead to lower resolution or inaccurate results.

BRIEF DESCRIPTION

In one embodiment, a method of estimating an electrical property of tissue using MR images is disclosed. The method includes generating complex values having real components and imaginary components. The complex values are associated with pixels in one or more MR images corresponding to a region of interest. The method further includes segmenting image into one more sub-regions for which the electrical property is constant and determining an estimated value of the electrical property for at least one of the one or more sub-regions based on a least squared error estimation applied to the complex values associated with at least one of the one or more sub-regions. In some embodiments, a conductivity image of the region of interest can be reconstructed by assigning estimated conductivity for each sub-region of constant properties. Similarly, in some embodiments, a relative permittivity image of the region of interest can be reconstructed by assigning estimated relative permittivity to each sub-region of constant properties.

The intensity (magnitude) of the image of the region of interest can be used to identify compartments or areas of constant electrical properties within the region of interest, by identifying contiguous regions of constant intensity. This may be done manually, by an expert user or may be done automatically using image segmentation algorithms. In automatic identification, software may use edge detection algorithms to detect sudden changes in image intensity and thereby determine the boundaries of compartments. Alternatively, an expert user may identify points (seed) within regions of constant intensity and the software may use region growing algorithm to capture all pixels of constant intensity near each seed point, thereby identifying the compartments of constant electrical properties.

In another embodiment, a non-transitory computer readable medium is disclosed that stores instructions. Execution of the instruction by a processing device causes the processing device to implement a method for estimating electrical properties of tissue using MR images. The method includes generating complex values having real components and imaginary components. The complex values are associated with pixels in one or more MR images corresponding to a region of interest. The method implemented upon execution of the instructions by the processing device further includes segmenting the region of interest into one or more sub-regions for which the electrical property is constant and determining an estimated value of the electrical property for at least one of the one or more sub-regions based on a least squared error estimation applied to the complex values associated with the at least one of the one or more sub-regions.

In yet another embodiment, a system for estimating electrical properties of tissue using MR images is disclosed. The system includes a non-transitory computer-readable medium and a processing device. The non-transitory computing readable medium stores complex values having real components and imaginary components. The complex values are associated with pixels in one or more MR images corresponding to a region of interest. The processing device is programmed to segment the region of interest into one or more sub-regions for which the electrical property is constant and determine an estimated value of the electrical property for at least one of the one or more sub-regions based on a least squared error estimation applied to the complex values associated with the at least one of the one or more sub-regions.

In some embodiments, the complex values can be defined by a square root of a product of a complex amplitude of a transmit RF magnetic field and a complex amplitude of a receive RF magnetic field. The product of the complex amplitude of the transmit RF magnetic field and the complex amplitude of the receive RF magnetic field can be obtained from a magnitude of an intensity associated with the MR images acquired using a gradient echo protocol and a phase associated with the phase of the MR images acquired using a spin echo scanning protocol. In some embodiments, the gradient echo image can have an excitation flip angle that is less than or equal to about ten degrees.

In some embodiments, the complex values can be defined by a complex amplitude of a transmit RF field, a magnitude of which is determined based on a transmit field mapping of the MR images acquired using a first scanning protocol and a phase of which is determined based on a phase associated with the phase of the MR images acquired using a second scanning protocol.

In some embodiments, the electrical property can be a permittivity of the tissue and the estimated value of the permittivity for the at least one of the one or more sub-regions can be determined based on the least squared error estimation by determining a first sum of a real component of the product of a Laplacian of the complex values and the complex conjugate of the complex values, determining a second sum of a product of the complex values and the complex conjugate of the complex values, multiplying the second sum by a constant value, and dividing the first sum by a product of the second sum and the constant value.

In some embodiments, the electrical property can be electrical conductivity of the tissue and the estimated value of the conductivity for the at least one of the one or more sub-regions can be determined based on the least squared error estimation by determining a first sum of an imaginary component of the product of a Laplacian of the complex values and the complex conjugate of the complex values, determining a second sum of a product of the complex values and the complex conjugate of the complex values, multiplying the second sum by a constant value, and dividing the first sum by a product of the second sum and the constant value.

In some embodiments, a map of the estimated value of the electrical property can be generated for the region of interest. The map can be employed in conjunction with dynamic contrast-enhanced imaging of the region of interest and malignant tissue can be distinguished from normal tissue based on values of the electrical property in the map.

Any combination or permutation of embodiments is envisaged. Other objects and features will become apparent from the following detailed description considered in conjunction with the accompanying drawings. It is to be understood, however, that the drawings are designed as an illustration only and not as a definition of the limits of the invention.

DETAILED DESCRIPTION

Exemplary embodiments provide a system and method to calculate the electrical properties of tissue (e.g., permittivity and/or conductivity) using a least squared error estimation based on a region of tissue having the same type (e.g., muscle, fat, bone). Exemplary embodiments of the present disclosure can allow for real time estimation of local Radio-Frequency (RF) power deposition or, in conjunction with mapping or images, provide diagnostically relevant information, such as for identifying tissue abnormality. At least one technical effect of some embodiments is the non-invasive estimation of the conductivity and/or permittivity of tissue using MRI in a clinically acceptable time frame. Other technical effects for some embodiments include evaluating RF safety, performing RF therapeutic methods, and diagnosing tissue abnormality using MRI mapping of conductivity and/or permittivity.

An intensity (magnitude) of pixels in an MR image of a region of interest can be used to identify compartments or areas (e.g., regions of tissue) of constant electrical properties within the region of interest, by identifying contiguous regions of constant intensity. In some embodiments, this may be achieved manually, by an expert user or may be achieved automatically using image segmentation algorithms. For embodiment in which regions of tissue are automatic identified, edge detection algorithms may be used to detect sudden changes in image intensity and thereby determine the boundaries of compartments. Alternatively, an expert user may identify points (seed) within regions of constant intensity and a region growing algorithm can be used to capture pixels of constant intensity near each seed point, thereby identifying the compartments or areas (e.g., regions of tissue) of constant electrical properties within the region of interest.

Figure 1:
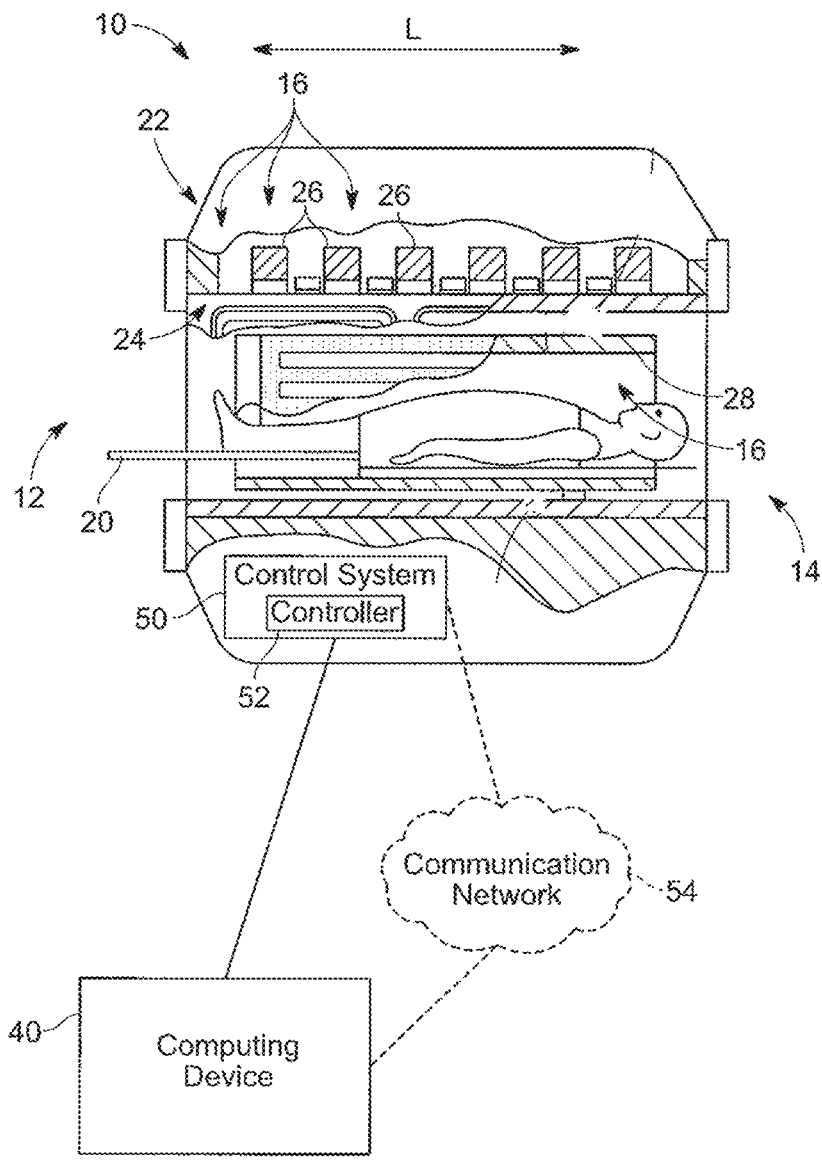
FIG. 1 illustrates an exemplary MRI scanner in accordance with exemplary embodiments of the present disclosure.

FIG. 1 is illustrative of a MRI scanner 10. The scanner 10 can generally extend longitudinally along a longitudinal axis L from a proximal end 12 to the distal end 14. The scanner 10 can include MRI components 16 forming an MRI scanner portion configured to acquire MR data. In some embodiments, the scanner 10 can be configured as a multi-modality imaging system. For example, the scanner 10 can be implemented as a combined medical imaging scanner configured to acquire MR image as well as Computed Tomography (CT) images, Positron Emission Tomography (PET) images, a Single Photon Emission Computed Tomography (SPECT) images, ultrasound images, and/or any other imaging modalities suitable for acquiring images of a subject.

The MRI components 16 can include a magnet assembly 22 and a gradient coil assembly 24, which can be implemented separately or as part of the magnet assembly 22. The magnet assembly 22 can include a polarizing main magnet 26 and a coil assembly 28, which can be implemented as a radio frequency (RF) coil and a phased array receive coil. The coil assembly 28 of the magnet assembly 22 can be configured to transmit stimulus pulses and to receive excitation pulses radiating from the subject in response to the stimulus pulses. The gradient assembly 24 can include one or more physical gradient coils (e.g., three gradient coils having orthogonal axes, X, Y, Z) to produce magnetic field gradients to spatially encode acquired MR data output from the scanner 10 according to a k-space or raw data matrix. In exemplary embodiments, one or more k-trajectories can be implemented, such as a Cartesian k-trajectory, spiral k-trajectory, cone k-trajectory, radial k-trajectory, and/or any other suitable k-trajectory.

In exemplary embodiments, the scanner 10 can include a control system 50 having processing device, e.g., controller 52, for controlling an operation of the scanner 10. The controller 52 of the control system 50 can be programmed to control an operation of the MRI components 16. While the control system 50 is depicted as being included in the scanner 10, those skilled in the art will recognize that the control system 50, or portions thereof, can be implemented separately and apart from the scanner 10 and can be communicatively coupled to the scanner 10. The control system 50 can be in communication with a computing device 40 such that the scanner 10 can be controlled, via a computing device 40 communicatively coupled to the control system 50, to transmit data and/or commands to the control system 50 to control an operation of the scanner 10. In some embodiments, the computing device 40 can be in communication with the control system 50 via a communications network 54. An exemplary computing device suitable for implementing the computing device 40 is shown in FIG. 7.

In exemplary embodiments, the computing device 40 can be configured and/or programmed to transmit instructions, commands, and/or requests to the control system 50 to control the MRI components 16 to perform scan sequences and can be programmed and/or configured to receive MR data or MR images from the control system 50. For example, RF pulses of a scan sequence for acquisition of MR images can have a timing, strength, and shape corresponding to a timing and length of a data acquisition window over which the MR data is to be acquired. Gradient pulses can be produced during the MR data acquisition by controlling one or more physical gradient coils (e.g., X, Y, Z coils) in a gradient coil assembly 24 to produce magnetic field gradients to spatially encode acquired MR data output from the scanner 10 in one or more lines of k-space. MR signals resulting from the excitation pulses, emitted by excited nuclei in a subject, can be sensed by the coil assembly 28, and can be provided to the computing system for processing. MR data can be collected and output as one or more sets of raw k-space data. The raw k-space data can be utilized in reconstruction (e.g., via Fourier transform) of MR image data by the computing device 40 and/or another device.

In exemplary embodiments, the computing device 40 (and/or the control system 50) can be programmed and/or configured to estimate electrical properties of a subject based on one or more MR data acquisitions. For example, the computing device 40 can be configured to estimate the permittivity and/or electrical conductivity of at least a portion of a subject. In one embodiment, in-vivo MR data measurements of living tissue, e.g., of a living human patient, can be used to estimate the permittivity and/or electrical conductivity of the living tissue. In exemplary embodiments, the computing device 40 can be programmed and/or configured to estimate the electrical properties of tissue, e.g., permittivity and/or conductivity, using a least squared error estimation described herein. In some embodiments, one or more complex images formed from MR scans acquired using different scanning protocol can be used by the computing device 40 when estimating the electrical properties of tissue with the embodiments of the least squared error estimation.

The permittivity and electrical conductivity of human tissue are related to a spatial distribution of the RF magnetic field by the following equations:

$$\nabla^2 B_1(m,n) + k^2(m,n) B_1(m,n) = 0, \tag{1}$$

where $$k^2(m,n) = \mu \epsilon_r(m,n) \epsilon_0 \omega^2 - i\mu\sigma(m,n)\omega \tag{2}$$

In the above equations, $B_1$ can represent the complex radio frequency (RF) transmit magnetic field $B_1^+$ inside the tissue at a given three dimensional location or can be associated with an intensity of a complex image given by a product of the complex amplitude of the radio frequency (RF) transmit magnetic field $B_1^+$ and complex amplitude of the RF receive magnetic field $B_1^-$ inside the tissue at the three dimensional location. The variable $k^2$ represents the complex wave number, which can be defined by the electrical properties of $k^2$ (magnetic permeability), $\epsilon_r$ (relative permittivity), $\sigma$ (conductivity) at a frequency $\omega = 2\pi f$. For mapping of tissue electrical properties, the magnetic permeability $\mu$ can be equated to the value in a vacuum, $\mu_0 = 4\pi \times 10^{-7}$ [H/m]. The constant $\epsilon_0 = 8.854 \times 10^{-12}$ [F/m] is the permittivity of a vacuum. The value m and n identify a pixel location for which the equations are evaluated.

In exemplary embodiments, the computing device 40 can be programmed and/or configured to consider a region of constant electrical properties (e.g., an area of tissue generally having the same electrical properties). The area can be identified by the intensity pixels in one or more MR images of the region, using for example, T1 weighted images. For example, the intensity of pixels in an MR image can be correlated to a type of tissue (e.g., muscle, bone, fat, etc.) such that a region of similar intensity identifies tissue of the same type. The electrical properties within this region can be represented by the variables $\epsilon$ and $\sigma$ in Eq. 1. If the values are exact, Eq. 1 is satisfied and the result is 0. Otherwise, there is an error term. This error term is $$E_{m,n}(\epsilon,\sigma) = \nabla^2 B1(m,n) + (\omega^2 \mu \epsilon - j\omega\mu\sigma) B1(m,n) \tag{4}$$

The squared error, summed over the region S of constant electrical properties can be given by the following mathematical expression:

$$\sum_{(m,n) \in S} |E_{m,n}(\epsilon, \sigma)|^2 = \sum_{(m,n) \in S} (E_{m,n}(\epsilon, \sigma))(E_{m,n}(\epsilon, \sigma))^* \tag{5}$$

The sum of squared error expression is quadratic in $\epsilon$ and $\sigma$. To find the minimum, the first derivative can be set to zero.

$$\frac{\partial}{\partial \varepsilon} \Sigma_{(m,n) \in S} |E_{m,n}(\varepsilon, \sigma)|^2 = 2\omega^2 \mu \Sigma_{(m,n) \in S} \text{Re}(\nabla^2 B1(m, n) \cdot B1(m, n)^*) + \quad (6)$$

$$2\varepsilon(\omega^2 \mu)^2 \Sigma_{(m,n) \in S} B1(m, n) \cdot B1(m, n)^*$$

$$= 0$$

Solving Eq. 6 for $\epsilon_r$ yields the following mathematical expression:

$$\varepsilon_r = -\frac{\Sigma_{(m,n) \in S} \text{Re}((\nabla^2 B1(m, n)) \cdot B1(m, n)^*)}{\omega^2 \mu \varepsilon_0 \Sigma_{(m,n) \in S} B1(m, n) \cdot B1(m, n)^*} \quad (7)$$

where $\epsilon = \epsilon_0 \epsilon_r$ is used to obtain relative permittivity and * is used to represent the complex conjugate.

Similarly, solving Eq. 6 for the conductivity yields the following mathematical expression:

$$\sigma = \frac{\Sigma_{(m,n) \in S} \text{Im}((\nabla^2 B1(m, n)) \cdot B1(m, n)^*)}{\omega \mu \Sigma_{(m,n) \in S} B1(m, n) \cdot B1(m, n)^*} \quad (8)$$

In some embodiments, the Laplacian in Eqs. 7 and 8 can be estimated using a curve fitting method. For example, a second order polynomial can be fitted to the $B_1$ data in a piecewise manner in each dimension (x, y and z) to obtain estimates of the Laplacian. In some embodiments, a multi-dimensional fitting can be used instead of a single dimensional fitting.

The computing device 40 can be programmed and/or configured to evaluate Eqs. 7 and 8 over the region S to compute the least squared error conductivity and permittivity values for the region S. The least squared error estimate of these electrical parameters can be robust to additive noise and can be implemented without discarding points as in a conventional B1 mapping pixel-by-pixel calculation of the electrical properties. Also, the Laplacian is estimated with only the minimum required number of points (no skip factors) and therefore, has better resolution compared to conventional B1 mapping techniques.

While exemplary embodiments of the least squared error estimation have been illustrated using Laplacian based calculations, those skilled in the art will recognize that integral-based calculations can be used. For example, Eq. 1 can start with the integral formulation and follow the same steps. In exemplary embodiments, the integral formulation of the least squared error estimation can provide improved noise immunity compared to the Laplacian based least squared error estimation. In exemplary embodiments, the least squared estimates based on the integral formulation can be expressed mathematically as follows:

$$\varepsilon_r = -\frac{\Sigma_{(m,n) \in S} \text{Re}\left(\oint_A \nabla B1(m, n) ds \cdot \int_V B1(m, n)^* dv\right)}{\omega^2 \mu \varepsilon_0 \Sigma_{(m,n) \in S} \int_V B1(m, n) dv \cdot \int_V B1(m, n)^* dv} \quad (9)$$

$$\sigma = \frac{\Sigma_{(m,n) \in S} \text{Im}\left(\oint_A \nabla B1(m, n) ds \cdot \int_V B1(m, n)^* dv\right)}{\omega \mu \Sigma_{(m,n) \in S} \int_V B1(m, n) dv \cdot \int_V B1(m, n)^* dv} \quad (10)$$

In some embodiments, B1 in Eqs. 1-10 can be a function of the intensity $I_{com}$ of complex images defined by the transmit RF magnetic field $B_1^+$ and the receive RF magnetic field $B_1^-$.

The complex images can be generated using different scanning protocols. For example, in some embodiments, low flip angle gradient echo imaging scans can be used to determine the product of the magnitudes of the transmit RF magnetic field $B_1^+$ and the receive RF magnetic field $B_1^-$ and, spin echo imaging scans can be used to determine the phase of the product of the transmit RF magnetic field $B_1^+$ and the receive RF magnetic field $B_1^-$, where the magnitude and phase define a complex amplitude of the product of the transmit RF magnetic field $B_1^+$ and the receive RF magnetic field $B_1^-$. The intensity $I_{com}$ of complex images can be defined using the following formulation for which the complex amplitude of an MR image is expressible as:

$$I = I_0 f(B_1^+) B_1^-. \quad (11)$$

where $I_0$ is a constant that depends on the tissue spin density and relaxation properties and is independent of the electrical properties and the RF field, and $f(B_1^+)$ is a function of the transmit RF field which depends on the imaging sequence. In case of a small-flip-angle gradient echo image, the image intensity satisfies the following mathematical expression:

$$|I_{GRE}| = I_0 |B_1^+ B_1^-|, \quad (12)$$

That is, the magnitude of the intensity of the gradient echo image ($I_{GRE}$) is equal to the magnitude of the product of the transmit RF field and the receive RF field multiplied by $I_0$. On the other hand, a spin echo image satisfies the following mathematical expression:

$$\angle I_{SE} = \angle (B_1^+ B_1^-). \quad (13)$$

That is, the phase of the spin echo image is equal to the phase of the product of the transmit RF field and the receive RF field. The phase of spin echo can be properly corrected against any artificial phase offset using a phantom scan, estimation, curve fitting, calibration, and/or any other suitable approaches to correcting for phase offset. In some embodiments, spin echo (SE) images are acquired of a low-conductivity, low-permittivity phantom that is substantially larger than an imaged object with the same scan prescription to calibrate out any scanner—or pulse sequence—specific image phase offset. This calibration can be performed when there is a reason to suspect change in such an offset and/or can be performed periodically. Using the image intensity from Eq. 12 and the phase from Eq. 13, a complex image can be formed combining the magnitude of the image intensity from the low flip angle (e.g., a flip angle that is less than or equal to ten degrees) gradient echo image with the phase from the spin echo image. This complex image $I_{COM}$ can be defined by one of the following mathematical expressions:

$$I_{COM} = \sqrt{|I_{GRE}| * e^{i * \angle I_{SE}}} \quad (14)$$

$$I_{COM} = \sqrt{B_1^+ B_1^-}, \quad (15)$$

where i represents the imaginary unit (i.e., $i^2 = -1$). The B1 in Eqs. 7-10 can be replaced with $I_{COM}$.

In some embodiments, B1 in Eqs. 1-10 can represent the complex amplitude of the radio frequency (RF) transmit magnetic field $B_1^+$ inside the tissue based on $B_1^+$ mapping of MR images. For example, $B_1^+$ mapping can be implemented to determine the $B_1^+$ field magnitude by acquiring an MR image (Image 1) with one Bloch-Siegert phase shift. In one embodiment, an off resonance image with positive frequency offset (e.g., +4 KHz from Larmor frequency) for each axial plane can be acquired, which in the illustrative embodiment includes three axial planes. Thereafter, for each axial plane, another image (Image 2) with another Bloch-Siegert phase shift can be acquired. In one embodiment, an off resonance image with negative frequency offset (e.g., −4 KHz from Larmor frequency) can be acquired for image 2. The images (Images 1 and 2) may be acquired using any suitable MRI image acquisition technique such as using spin echo or gradient echo imaging. After acquiring the images, the phase difference of the two images (Images 1 and 2) for each plane can be determined, such as by using a suitable pixel subtraction method.

The $B_1^+$ map for each image slice can be determined by multiplying the phase difference by a scaling factor to realize the $B_1^+$ maps (magnitude) for each image slice. It should be noted that any suitable method for B1 mapping may be used to determine the B1 magnitude. For example, in some embodiments, $B_1^+$ mapping can be performed using a Bloch-Siegert shift may be used as described in U.S. Patent Application Publication 2010/0315084, entitled "System, Method, And Apparatus For Magnetic Resonance RF-Field Measurement", the disclosure of which is incorporated herein in its entirety. In some embodiments, other $B_1^+$ mapping techniques can be used, for example, dual flip angle or multiple flip angle techniques.

The $B_1^+$ phase estimate can be determined for each axial plane by acquiring spin echo images of the subject. The spin echo images can be acquired using any suitable spin echo imaging technique. For example, the spin echo images can be acquired using a switched mode, quadrature coil (e.g., a birdcage type body coil or transmit/receive head coil). Thereafter, a phase map is generated using the real and imaginary spin echo images of each plane. Alternatively, the phase image provided by scanner can be used.

In exemplary embodiments, MR data can be acquired from quadrature transmit/receive coils. The $B_1^+$ magnitude estimated using gradient echo images and $B_1^-$ phase estimated using spin echo images are more accurate when such coil is used.

A system introduced linear phase shift, if any, can be removed. For example, some MRI systems introduce phase variation during image acquisition, which is removed or corrected so that only the subject (or sample) induced or introduced phase variation is determined. The system introduced phase shift may be removed, for example, by comparing the spin echo images and phantom images acquired by the MRI system. Thus, the phantom image is used as a reference image and compared to the spin echo images of the subject. In one embodiment, the linear phase variation for each line of the images is determined and fit to curve (e.g., a straight line fit) and then removed (e.g., subtracted from the images). Removing the system introduced phase variation results in a determination of the phase shift in the spin echo images due to the subject.

The $B_1^+$ phase for each axial plane is determined. For example, in one embodiment, for each axial plane, the determined phase is divided by two and conjugated to obtain the $B_1^+$ phase. It should be noted that the $B_1^+$ phase estimate described above is merely for illustration and any suitable $B_1^+$ phase estimation technique may be used.

The $B_1^+$ magnitude and phase as described above are used to determine the complex $B_1^+$ field, for example, by multiplying the magnitude by the phase. Exemplary methods for $B_1^+$ mapping are described in more detail in U.S. patent application Ser. No. 13/174,010, entitled "System and Method for Determining Electrical Properties Using Magnetic Resonance Imaging" and filed on Jun. 30, 2011, the disclosure of which is incorporated by reference herein in its entirety. The complex $B_1^+$ field can replace the B1 in Eqs. 1-10 to estimate the electrical properties permittivity and conductivity using the least squared error estimation.

Figure 2:
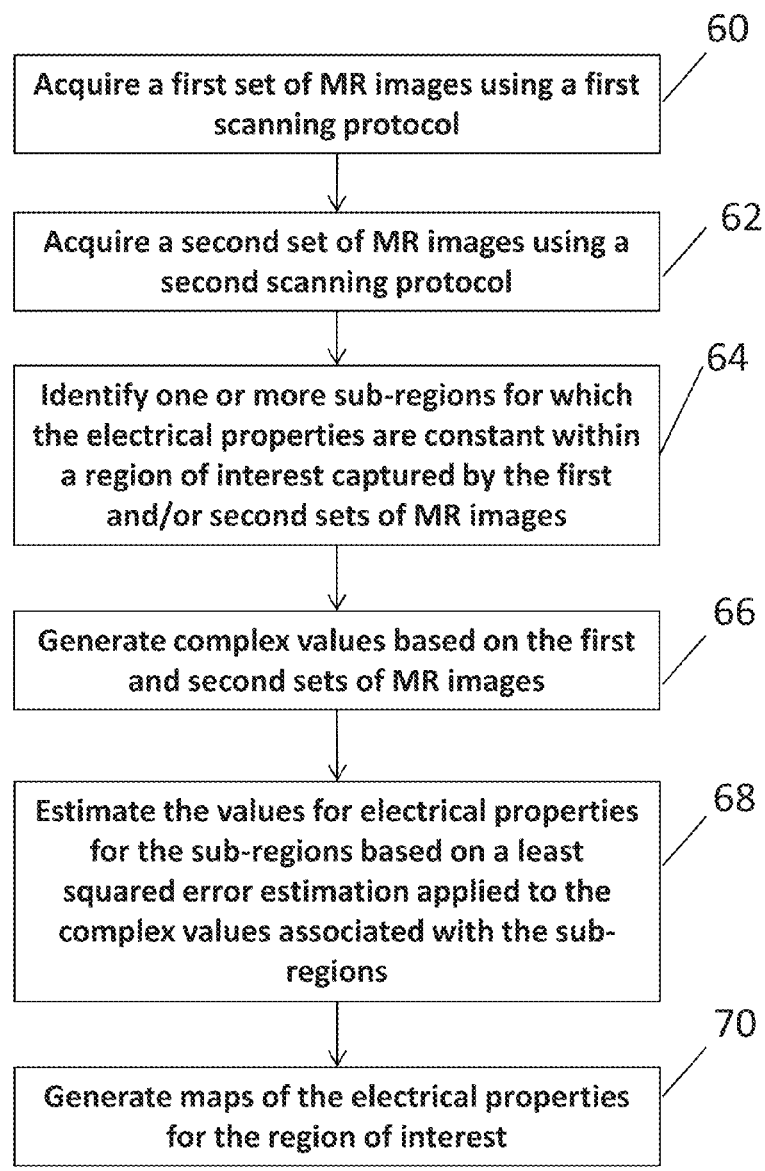
FIG. 2 is a flowchart illustrating an exemplary process for estimating electrical properties of tissue using a complex image.

FIG. 2 is a flowchart of an exemplary process implemented by the computing device 40 (FIG. 1) for estimating electrical properties (e.g., permittivity and electrical conductivity) of tissue using an exemplary embodiment of the least squared error estimation. To begin, N slices are acquired for at least two scanning protocols with a slice spacing S centered around the slice on which measurement of the electrical properties is desired (target slice). In exemplary embodiments, at least three slices (e.g., axial planes) are acquired (N≥3) and the slice spacing is generally uniform, e.g., approximately 3 mm spacing in some embodiments. The region of constant electrical properties is identified by the images that are acquired. For example, spin echo images can be used to estimate B1 phase. When the spin echo image is obtained, segmentation of the image can be based on the intensity (magnitude) of spin echo image. The regions of constant electrical properties are identified after this segmentation.

In the present embodiment, a first set of MR images of a region of interest are acquired on the N slices by the scanner 10 using a first scanning protocol (e.g., gradient echo scans) in response to instructions received from the computing device in step 60, and a second set of MR images of the region of interest are acquired on the same slices by the scanner 10 using a second scanning protocol (e.g., spin echo) in response to instructions received from the computing device in step 62.

In step 64, one or more sub-regions of tissue (e.g., compartments or areas) within the region of interest can be identified to segment the MR images into sub-regions formed of the same tissue type and for which the electrical properties are constant. Each of the one or more sub-regions can be identified within the region of interest based on an intensity of the pixels in the MR images. For example, pixels having the same intensity can correspond to the same tissue type, and therefore, can have the same electrical properties. In exemplary embodiments, contiguous areas of constant intensity can be identified to generate the sub-regions (e.g., compartments or areas). In some embodiments, this may be achieved manually, by an expert user or may be achieved automatically using image segmentation algorithms. For embodiment in which sub-regions are automatic identified, edge detection algorithms may be used to detect sudden changes in image intensity and thereby determine the boundaries of compartments. Alternatively, an expert user may identify points (seed) within regions of constant intensity and a region growing algorithm can be used to capture pixels of constant intensity near each seed point, thereby identifying the sub-regions (e.g., compartments or areas) of constant electrical properties within the region of interest. The first and/or second sets of MR images can be used to identify the sub-regions within the region of interest. One exemplary segmentation process that can be used is described, for example, in U.S. patent application Ser. No. 13/618,079, entitled "Method And System For Correction of Lung Density Variation in Positron Emission Tomography Using Magnetic Resonance Imaging", the disclosure of which is incorporated herein in its entirety.

In step 66, the first and second sets of MR images are used to generate complex values $B_1$ having a magnitude corresponding to the intensity of the MR images for the first set of MR images and a phase corresponding to the phase of the second set of images. As one example, in one embodiment, the complex value $B_1$ can correspond to an amplitude of the intensity of a complex image (e.g., $I_{COM}$) determined using the magnitude of the transmit RF magnetic field $B_1^+$ and the receive RF magnetic field $B_1^-$ from the first set of MR images and a phase of the transmit RF magnetic field $B_1^+$ and the receive RF magnetic field $B_1^-$ from the second set of MR images. As another example, in one embodiment, the complex value $B_1$ can be determined by a complex $B_1^+$ field generated using $B_1^+$ mapping of the first and second sets of MR images to define a complex $B_1^+$ field.

After the complex value $B_1$ is determined, in step 68, the computing device can be programmed and/or configured to estimate values for the electrical property for the one or more sub-regions identified in the target slice by evaluating Eqs. 7 and 8 and/or Eqs. 9 and 10. The computing device can be programmed and/or configured to estimate the electrical property based on a summation across each of the one or more sub-region such that the electrical properties are determined based on a group of pixels corresponding to each of the sub-regions as opposed to determining the electrical properties associated with the region of interest on a pixel-by-pixel basis. Electrical property maps can be generated for the region of interest in the target slice in step 70 using the estimated electrical property of each of the sub-regions, and the computing device 40 can be programmed and/or configured to output the electrical property maps to an output device, such as a display device or a printer, and/or can stored the electrical property maps in a non-transitory computer-readable medium. For example, the electrical property maps can be rendered on a display unit (FIG. 7) so that an operator may view and/or analyze the electrical properties of tissue associated with the acquired images.

Figures 3A, 3B:
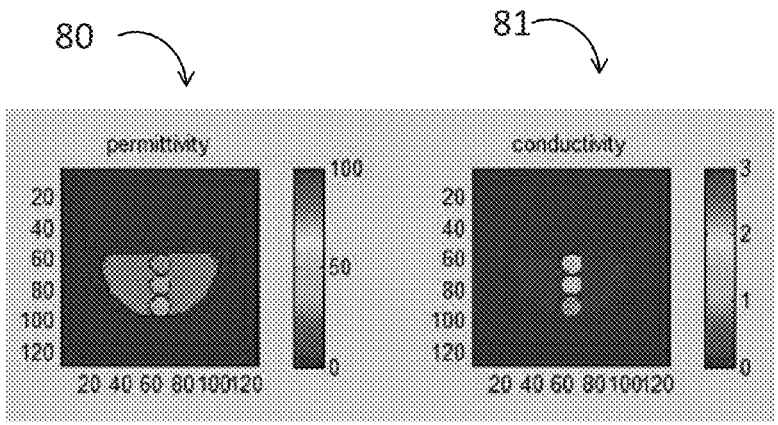
FIG. 3A illustrates a map of relative permittivity of phantoms using an exemplary embodiment of the process of FIG. 2.
FIG. 3B illustrates a map of electrical conductivity of phantoms using an exemplary embodiment of the process of FIG. 2.
Figures 4A, 4B:
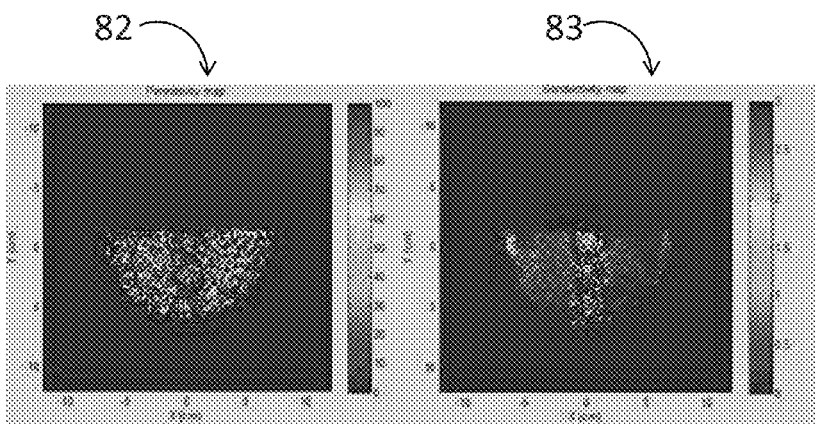
FIG. 4A illustrate a map of relative permittivity of phantoms using a conventional B1 mapping process.
FIG. 4B illustrates a map of an electrical conductivity of phantoms using a conventional B1 mapping process.

FIGS. 3A and 3B illustrate exemplary electrical property maps 80 and 81, respectively. FIGS. 4A and 4B illustrate exemplary electrical property maps 82 and 83. The maps 80 and 82 correspond to a relative permittivity and the maps 81 and 83 correspond to conductivity. The relative permittivity and conductivity were measured in a phantom experiment to demonstrate an application of exemplary embodiments. A half sphere phantom was prepared with three spheres inside. The half sphere and the three spheres were filled with various concentrations of NaCl in distilled water given by Table 1 below. The composite phantom was imaged in a head coil, $B_1$ magnitude and phase data were acquired and electrical properties were reconstructed on a pixel by pixel basis (FIGS. 4A and 4B) and an exemplary embodiment of least squared error estimation (FIGS. 3A and 3B). The least squared error calculations shown in FIGS. 3A and 3B omitted the pixels at the boundary of materials to avoid errors due to $B_1$ transitions at material boundaries.

Figure 5:
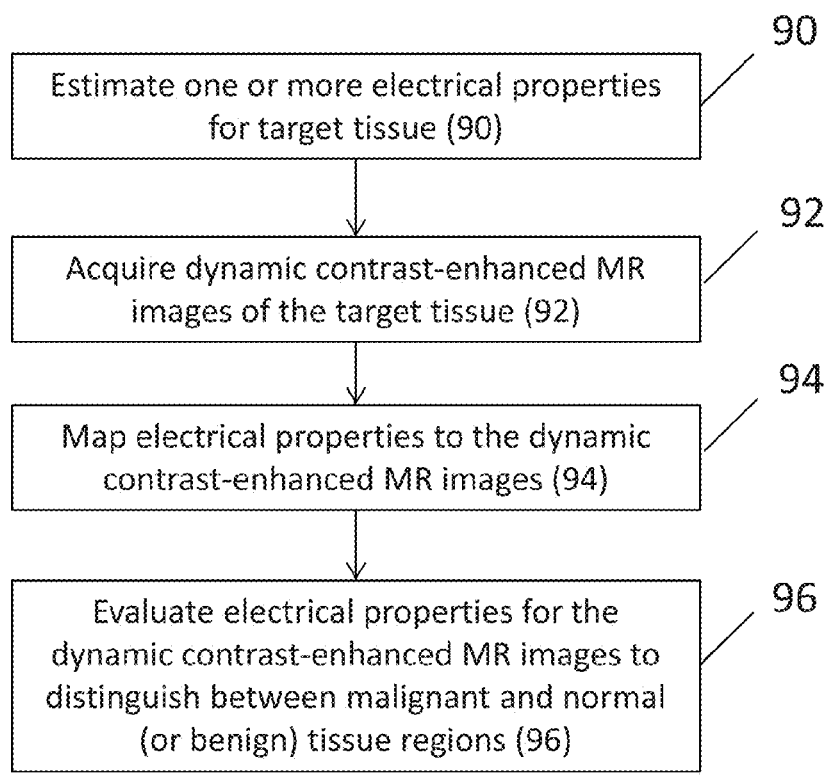
FIG. 5 is a flowchart of an exemplary process for discriminating between malignant tissue and normal tissue based on an estimation of electrical properties using an exemplary embodiment of the process of FIG. 2.

FIG. 5 is a flowchart of an exemplary process for discriminating between malignant tissue and normal (or benign) tissue in acquired MR images. In step 90, one or more electrical properties (e.g., permittivity and conductivity) are estimated for target tissue (e.g., region of interest) based on an embodiment of the process described herein with reference to FIG. 2. Additionally, in step 92, dynamic contrast-enhanced MR imaging of the target tissue is acquired. In step 94, the values of one or more electrical properties are mapped to the dynamic contrast-enhanced MR images to associate the values of the one or more electrical properties with corresponding pixels of the dynamic contrast-enhanced MR images. In step 96, the values of the electrical properties are evaluated for the dynamic contrast-enhanced MR images to distinguish between malignant and normal (or benign) tissue regions. For example, it may be difficult to distinguish whether a tumor is malignant or benign using the dynamic contrast-enhanced MR images. By mapping or superimposing the estimated values of the electrical properties to the dynamic contrast-enhanced MR images, the relationship between the electrical properties and composition of tissue can be used to determine whether the tumor is malignant. For example, malignant tissue has been shown to have a permittivity value that is greater than the permittivity of normal (or benign) tissue. Furthermore, malignant tissue has been shown to have a conductivity value that is greater than the conductivity of normal (or benign) tissue.

Figure 6:
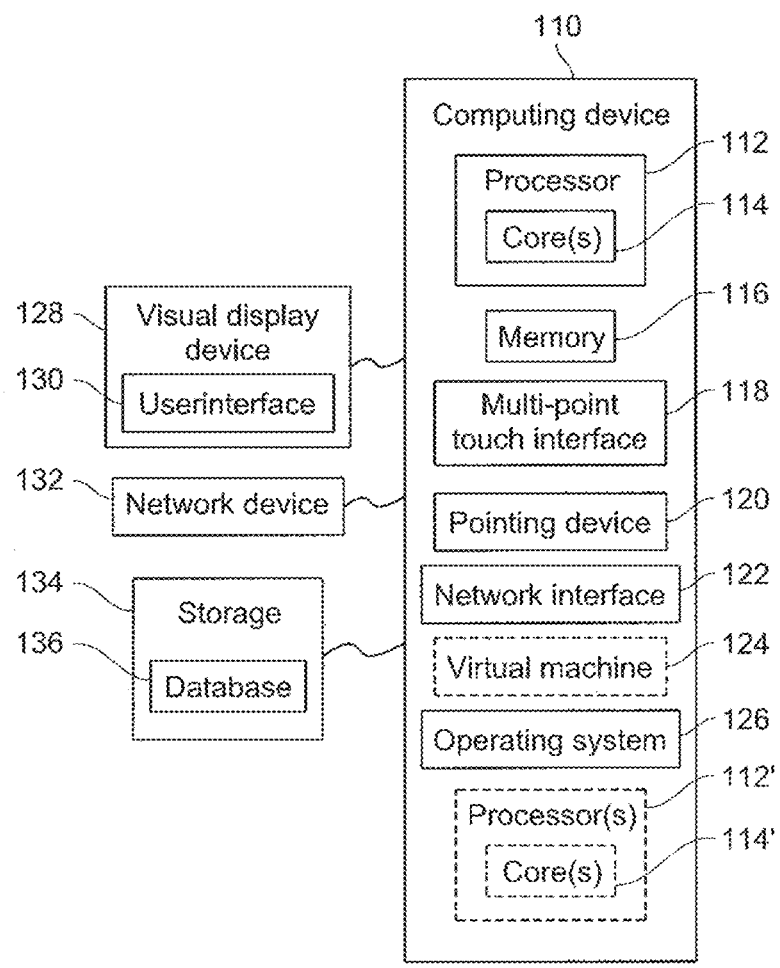
FIG. 6 is an exemplary computing device programmed and/or configured to implement embodiments of the present disclosure.

FIG. 6 is a block diagram of an exemplary computing device 110 that may be used to implement exemplary embodiments of the computing device 40. The computing device 110 includes one or more non-transitory computer-readable media for storing one or more computer-executable instructions or software for implementing exemplary embodiments. The non-transitory computer-readable media may include, but are not limited to, one or more types of hardware memory, non-transitory tangible media (for example, one or more magnetic storage disks, one or more optical disks, one or more flash drives), and the like. For example, memory 116 included in the computing device 110 may store computer-readable and computer-executable instructions or software for interface with and/or controlling an operation of the scanner 10. The computing device 110 also includes configurable and/or programmable processor

TABLE 1

Permittivity and conductivity (S/m) of phantom fluids - measured from Agilent probe, average values from pixel by pixel calculation and results from Least squared error method.

| Compartment | Fluid | Measured at 200 MHz (Agilent probe) | | Average values from Laplacian | | Least squared error results | |
|---|---|---|---|---|---|---|---|
| Outer | 0.5 g/L NaCl | 78.2 | 0.16 S/m | 59 | 0.44 S/m | 79 | 0.13 S/m |
| Top ball | 9 g/L NaCl | 77 | 1.45 S/m | 46.7 | 1.39 S/m | 77 | 1.33 S/m |
| Middle ball | 5 g/L NaCl | 77 | 0.87 S/m | 52.2 | 1.54 S/m | 74.5 | 1.12 S/m |
| Bottom ball | 3.7 g/L NaCl | 75 | 0.65 S/m | 51.9 | 1.45 S/m | 72.8 | 0.81 S/m |

The regions of constant properties were identified manually, using the intensity image and knowledge of the phantom as a guide. As shown in FIGS. 3A and 3B, estimation of the electrical properties for a region have generally constant values for the permittivity and conductivity σ can be accurately estimated using an exemplary embodiment of the least squared error estimation described herein as compared to an estimation of the values of the electrical properties shown in FIGS. 4A and 4B obtained using conventional $B_1$ mapping techniques.

112 and associated core 114, and optionally, one or more additional configurable and/or programmable processing devices, e.g., processor(s) 112' and associated core(s) 114' (for example, in the case of computer systems having multiple processors/cores), for executing computer-readable and computer-executable instructions or software stored in the memory 116 and other programs for controlling system hardware. Processor 112 and processor(s) 112' may each be a single core processor or multiple core (114 and 114') processor.

Virtualization may be employed in the computing device 110 so that infrastructure and resources in the computing device may be shared dynamically. A virtual machine 124 may be provided to handle a process running on multiple processors so that the process appears to be using only one computing resource rather than multiple computing resources. Multiple virtual machines may also be used with one processor.

Memory 116 may include a computer system memory or random access memory, such as DRAM, SRAM, EDO RAM, and the like. Memory 116 may include other types of memory as well, or combinations thereof.

A user may interact with the computing device 110 through a visual display device 128, such as a computer monitor, which may display one or more user interfaces 130 that may be provided in accordance with exemplary embodiments. The computing device 110 may include other I/O devices for receiving input from a user, for example, a keyboard or any suitable multi-point touch interface 118, a pointing device 120 (e.g., a mouse). The keyboard 118 and the pointing device 120 may be coupled to the visual display device 128. The computing device 110 may include other suitable conventional I/O peripherals.

The computing device 110 may also include one or more storage devices 134, such as a hard-drive, CD-ROM, or other computer readable media, for storing data and computer-readable instructions and/or software that interface with and/or control an operation of the scanner 10 described herein and/or to implement exemplary processes described herein with reference to FIGS. 2, 5, and 6. Exemplary storage device 134 may also store one or more databases for storing any suitable information required to implement exemplary embodiments. For example, exemplary storage device 134 can store one or more databases 136 for storing information, such as scan sequences, MR data, MR images, estimation of electrical properties, electrical property maps, and/or any other information that can be used to implement exemplary embodiments of the present disclosure. The databases may be updated by manually or automatically at any suitable time to add, delete, and/or update one or more items in the databases.

The computing device 110 can include a network interface 122 configured to interface via one or more network devices 132 with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. The network interface 122 may include a built-in network adapter, network interface card, PCMCIA network card, card bus network adapter, wireless network adapter, USB network adapter, modem or any other device suitable for interfacing the computing device 110 to any type of network capable of communication and performing the operations described herein. Moreover, the computing device 110 may be any computer system, such as a workstation, desktop computer, server, laptop, handheld computer, tablet computer, or other form of computing or telecommunications device that is capable of communication and that has sufficient processor power and memory capacity to perform the operations described herein.

The computing device 110 may run any operating system 126, such as any of the versions of the Microsoft® Windows® operating systems, the different releases of the Unix and Linux operating systems, any version of the MacOS® for Macintosh computers, any embedded operating system, any real-time operating system, any open source operating system, any proprietary operating system, or any other operating system capable of running on the computing device and performing the operations described herein. In exemplary embodiments, the operating system 126 may be run in native mode or emulated mode. In an exemplary embodiment, the operating system 126 may be run on one or more cloud machine instances.

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a plurality of system elements, device components or method steps, those elements, components or steps may be replaced with a single element, component or step. Likewise, a single element, component or step may be replaced with a plurality of elements, components or steps that serve the same purpose. Moreover, while exemplary embodiments have been shown and described with references to particular embodiments thereof, those of ordinary skill in the art will understand that various substitutions and alterations in form and detail may be made therein without departing from the scope of the invention. Further still, other aspects, functions and advantages are also within the scope of the invention.

Exemplary flowcharts are provided herein for illustrative purposes and are non-limiting examples of methods. One of ordinary skill in the art will recognize that exemplary methods may include more or fewer steps than those illustrated in the exemplary flowcharts, and that the steps in the exemplary flowcharts may be performed in a different order than the order shown in the illustrative flowcharts.

The invention claimed is:

1. A method of estimating an electrical property of tissue using MR images comprising:
   generating complex values having real components and imaginary components, the complex values being associated with pixels in one or more MR images corresponding to a region of interest;
   segmenting the region of interest into one or more sub-regions for which the electrical property is constant; and
   determining an estimated value of the electrical property for at least one of the one or more sub-regions based on a least squared error estimation applied to the complex values associated with the at least one of the one or more sub-regions.

2. The method of claim 1, wherein the complex values are defined by a square root of a product of a complex amplitude of a transmit RF magnetic field and a complex amplitude of a receive RF magnetic field.

3. The method of claim 2, wherein the product of the complex amplitudes of the transmit RF magnetic field and the receive RF magnetic field corresponds to a magnitude of an intensity associated with the MR images acquired using gradient echo protocol and a phase associated with a phase of the MR images acquired using a spin echo scanning protocol.

4. The method of claim 2, wherein the gradient echo image has an excitation flip angle that is less than or equal to about ten degrees.

5. The method of claim 1, wherein the complex values are defined by a complex amplitude of a transmit RF field, a magnitude of which is determined based on a transmit field mapping of the MR images acquired using a first scanning protocol and a phase of which is determined based on a phase associated with a phase of the MR images acquired using a second scanning protocol.

6. The method of claim 1, wherein the electrical property is a permittivity of the tissue and wherein determining the estimated value of the permittivity for the at least one of the sub-regions based on the least squared error estimation further comprises:
- determining a first sum of a real component of the product of a Laplacian of the complex values and the complex conjugate of the complex values;
- determining a second sum of a product of the complex values and the complex conjugate of the complex values;
- multiplying the second sum by a constant value; and
- dividing the first sum by a product of the second sum and the constant value.

7. The method of claim 1, wherein the electrical property is electrical conductivity of the tissue and wherein determining the estimated value of the conductivity for the at least one of the sub-regions based on the least squared error estimation further comprises:
- determining a first sum of an imaginary component of the product of a Laplacian of the complex values and the complex conjugate of the complex;
- determining a second sum of a product of the complex values and the complex conjugate of the complex values;
- multiplying the second sum by a constant value; and
- dividing the first sum by a product of the second sum and the constant value.

8. The method of claim 1, further comprising generating a map of the electrical property for the region of the interest based on the estimated value of the electrical property for the one or more sub-regions.

9. The method of claim 8, further comprising:
- employing the map in conjunction with dynamic contrast-enhanced imaging of the region of interest; and
- distinguishing between malignant tissue and normal tissue based on values of the electrical property in the map.

10. A non-transitory computer readable medium storing instructions, wherein execution of the instruction by a processing device causes the processing device to implement a method for estimating electrical properties of tissue using MR images comprising:
- generating complex values having real components and imaginary components, the complex values being associated with pixels in one or more MR images corresponding to a region of interest;
- segmenting the region of interest into one or more sub-regions for which the electrical property is constant; and
- determining an estimated value of the electrical property for at least one of the one or more sub-regions based on a least squared error estimation applied to the complex values associated with the at least one of the one or more sub-regions.

11. The medium of claim 10, wherein the complex values arc defined by a square root of a product of a complex amplitude of a transmit RF magnetic field and a complex amplitude of a receive RF magnetic field.

12. The medium of claim 10, wherein the complex amplitude of the transmit RF magnetic field and the complex amplitude of a receive RF magnetic field correspond to a magnitude of an intensity associated with the MR images acquired using gradient echo protocol and a phase associated with an intensity of the MR images acquired using a spin echo scanning protocol.

13. The medium of claim 10, wherein the complex values are defined by a complex amplitude of a transmit RF field, a magnitude of which is determined based on a transmit field mapping of the MR images acquired using a first scanning protocol and a phase of which is determined based on a phase associated with an intensity of the MR images acquired using a second scanning protocol.

14. The medium of claim 10, wherein the electrical property is a permittivity of the tissue and wherein determining the estimated value of the permittivity for the at least one of the one or more sub-regions based on the least squared error estimation further comprises:
- determining a first sum of a real component of the product of a Laplacian of the complex values and the complex conjugate of the complex values;
- determining a second sum of a product of the complex values and the complex conjugate of the complex values;
- multiplying the second sum by a constant value; and
- dividing the first sum by a product of the second sum and the constant value.

15. The medium of claim 10, wherein the electrical property is electrical conductivity of the tissue and wherein determining the estimated value of the conductivity for the at least one of the one or more sub-regions based on the least squared error estimation further comprises:
- determining a first sum of an imaginary component of the product of a Laplacian of the complex values and the complex conjugate of the complex;
- determining a second sum of a product of the complex values and the complex conjugate of the complex values;
- multiplying the second sum by a constant value; and
- dividing the first sum by a product of the second sum and the constant value.

16. A system for estimating electrical properties of tissue using MR images comprising:
- a non-transitory computing readable medium storing complex values having real components and imaginary components, the complex values being associated with pixels in one or more MR images corresponding to a region of interest; and
- a processing device programmed to segment the region of interest into one or more sub-regions for which electrical property is constant and determine an estimated value of the electrical property for at least one of the one or more sub-regions based on a least squared error estimation applied to the complex values associated with the at least one of the one or more sub-regions.

17. The system of claim 16, wherein the complex values are defined by a square root of a product of a complex amplitude of a transmit RF magnetic field and a complex amplitude of a receive RF magnetic field.

18. The system of claim 16, wherein the complex amplitude of the transmit RF magnetic field and the complex amplitude of a receive RF magnetic field correspond to a magnitude of an intensity associated with the MR images acquired using gradient echo protocol and a phase associated with an intensity of the MR images acquired using a spin echo scanning protocol.

19. The system of claim 16, wherein the complex values are defined by a complex amplitude of a transmit RF field, a magnitude of which is determined based on a transmit field mapping of the MR images acquired using a first scanning protocol and a phase of which is determined based on a phase associated with an intensity of the MR images acquired using a second scanning protocol.

20. The system of claim 16, wherein the electrical property is at least one of permittivity and conductivity of the tissue and wherein determining the estimated value of the at least one of permittivity and conductivity for the at least one of the one or more sub-regions based on the least squared error estimation further comprises:

determining a first sum of a real component or an imaginary component of the product of a Laplacian of the complex values and the complex conjugate of the complex values;
determining a second sum of a product of the complex values and the complex conjugate of the complex values;
multiplying the second sum by a constant value; and
dividing the first sum by a product of the second sum and the constant value.

* * * * *